US008383677B2

(12) United States Patent
Kontani et al.

(10) Patent No.: US 8,383,677 B2
(45) Date of Patent: Feb. 26, 2013

(54) NERVE-REGENERATING AGENT

(75) Inventors: Masanori Kontani, Mishima-gun (JP); Yoshiyuki Ishikura, Mishima-gun (JP); Noriko Oosumi, Sendai (JP); Motoko Maekawa, Sendai (JP)

(73) Assignees: Suntory Holdings Limited, Osaka-shi, Osaka (JP); Tohoku University, Sendai-shi, Miyagi (JP)

( * ) Notice: Subject to any disclaimer, the term of this patent is extended or adjusted under 35 U.S.C. 154(b) by 0 days.

(21) Appl. No.: 12/520,989

(22) PCT Filed: Dec. 27, 2007

(86) PCT No.: PCT/JP2007/075403
§ 371 (c)(1),
(2), (4) Date: Jun. 24, 2009

(87) PCT Pub. No.: WO2008/081989
PCT Pub. Date: Jul. 10, 2008

(65) Prior Publication Data
US 2010/0016433 A1 Jan. 21, 2010

(30) Foreign Application Priority Data
Dec. 28, 2006 (JP) .................................. 2006-355854

(51) Int. Cl.
*A61K 31/225* (2006.01)
*A61K 31/22* (2006.01)
*A61K 31/20* (2006.01)
*A61K 31/70* (2006.01)
*A61K 31/685* (2006.01)
*A61K 31/66* (2006.01)

(52) U.S. Cl. ............ 514/547; 514/560; 514/25; 514/75; 514/77; 514/78; 514/549

(58) Field of Classification Search .................. 514/114, 514/560, 547, 549, 25, 75, 77, 78
See application file for complete search history.

(56) References Cited

U.S. PATENT DOCUMENTS

| | | | |
|---|---|---|---|
| 4,526,902 A | 7/1985 | Rubin | |
| 4,668,704 A | 5/1987 | Hollander et al. | |
| 5,198,468 A | 3/1993 | Horrobin | |
| 5,583,019 A | 12/1996 | Barclay | |
| 5,866,703 A | 2/1999 | Horrobin et al. | |
| 5,902,807 A | 5/1999 | Haapalinna et al. | |
| 6,034,130 A | 3/2000 | Wang et al. | |
| 6,069,138 A | 5/2000 | Ponroy | |
| 6,080,787 A | 6/2000 | Carlson et al. | |
| 6,225,444 B1 * | 5/2001 | Shashoua | 530/345 |
| 6,417,233 B1 * | 7/2002 | Sears et al. | 514/549 |
| 2002/0040058 A1 | 4/2002 | Kiliaan et al. | |
| 2004/0219208 A1 | 11/2004 | Kawamura et al. | |
| 2004/0266874 A1 | 12/2004 | Akimoto et al. | |
| 2006/0057185 A1 | 3/2006 | Akimoto et al. | |
| 2006/0088573 A1 | 4/2006 | Ishikura et al. | |
| 2006/0217368 A1 | 9/2006 | Morishita et al. | |

FOREIGN PATENT DOCUMENTS

| | | |
|---|---|---|
| CA | 2109777 | 5/1994 |
| CA | 2596241 | 12/1994 |
| CA | 2 512 133 | 5/2005 |
| CN | 1155982 A | 8/1997 |
| CN | 1175976 | 3/1998 |
| CN | 1205839 | 1/1999 |
| EP | 0 234 733 B1 | 11/1991 |
| EP | 0 713 653 A1 | 5/1996 |
| EP | 1 894 472 | 10/1997 |
| EP | 10-191886 | 7/1998 |
| EP | 0 965 578 | 12/1999 |
| EP | 1 239 022 | 9/2002 |
| EP | 1 419 768 | 5/2004 |
| GB | 0111282.0 | 5/2001 |
| JP | 06256179 A | 9/1994 |
| JP | 8-143454 | 6/1996 |
| JP | 08214891 | 8/1996 |
| JP | 8-511533 | 12/1996 |
| JP | 09-023817 | 1/1997 |
| JP | 09030962 A | 2/1997 |
| JP | 10-101568 | 4/1998 |
| JP | 10-155459 | 6/1998 |
| JP | 11034236 A | 2/1999 |
| JP | 2000-8074 | 1/2000 |
| JP | 2000-516261 | 12/2000 |
| JP | 2001-31586 A | 2/2001 |
| JP | 2003-48831 | 2/2003 |
| JP | 2003-504333 | 2/2003 |
| JP | 2003-113120 | 4/2003 |
| JP | 2006-502196 | 1/2006 |
| JP | 2006/076948 | 3/2006 |
| JP | 2006-83134 | 3/2006 |
| JP | 2006-83136 | 3/2006 |
| JP | 2006-521369 | 9/2006 |

(Continued)

OTHER PUBLICATIONS

Paoli et al. IT 1299623, 2000, abstract only, Caplus, AN 2002:39793.*
Search Report dated Mar. 4, 2008 for International Application No. PCT/JP2007/075403 filed Dec. 27, 2007.
Susumu Kotani et al., "Dietary supplementation of arachidonic and docosahexanoic acids improves cognitive dysfunction," 2006, pp. 159-164, vol. 56, Neuroscience Research, Limerick, Ireland.
Yoshimura et al., "FGF-2 regulation of neurogenesis in adult hippocampus after brain injury," PNAS, May 8, 2001, vol. 98, No. 10, pp. 5874-5879.
Nakatomi et al., "Regeneration of Hippocampal Pyramidal Neurons after Ischemic Brain Injury by Recruitment of Endogenous Neural Progenitors," Cell, vol. 110, Aug. 23, 2002, pp. 429-441.
Kawakita et al., "Docosahexaenoic Acid Promotes Neurogenesis in Vitro and in Vivo," Neuroscience, 2006, vol. 139, pp. 991-997.
Hirano et al., "Influence of Taurine Load on Neural Development," Program of 173rd Meeting of the Essential Amino Acid Research Council, 2003, p. 1 (with partial English-language translation).
European Search Report dated Jan. 27, 2010 in EP Application No. 07860598.7.

(Continued)

*Primary Examiner* — Shengjun Wang
(74) *Attorney, Agent, or Firm* — Drinker Biddle & Reath LLP

(57) ABSTRACT

A nerve-regenerating agent comprising, as an active ingredient, arachidonic acid and/or a compound containing arachidonic acid as a constituent fatty acid.

6 Claims, 1 Drawing Sheet

FOREIGN PATENT DOCUMENTS

| | | |
|---|---|---|
| JP | 2007-8863 | 1/2007 |
| WO | 94/28913 | 12/1994 |
| WO | WO 94/28891 | 12/1994 |
| WO | 96/10922 | 4/1996 |
| WO | WO 96/21037 | 7/1996 |
| WO | 98/50052 | 11/1998 |
| WO | WO 00/21524 | 4/2000 |
| WO | 01/03696 | 1/2001 |
| WO | WO-0124645 A1 | 4/2001 |
| WO | 01/85158 A2 | 11/2001 |
| WO | 01/91745 A2 | 12/2001 |
| WO | WO 01/97793 A2 | 12/2001 |
| WO | 02/02105 | 1/2002 |
| WO | WO 02/19839 | 3/2002 |
| WO | WO-0184961 A3 | 8/2002 |
| WO | 02/089787 | 11/2002 |
| WO | 02/102394 A2 | 12/2002 |
| WO | 03/004667 | 1/2003 |
| WO | 03/013497 A1 | 2/2003 |
| WO | WO-03013497 A1 | 2/2003 |
| WO | 03/092673 A1 | 11/2003 |
| WO | 2004/024136 A1 | 3/2004 |
| WO | 2004/024930 A2 | 3/2004 |
| WO | 2004/028529 | 4/2004 |
| WO | 2004/084882 A1 | 10/2004 |
| WO | WO 2004/091663 A1 | 10/2004 |
| WO | 2005/018632 | 3/2005 |
| WO | 2005/037848 A2 | 4/2005 |
| WO | 2005/072306 | 8/2005 |
| WO | 2006/030552 | 3/2006 |

OTHER PUBLICATIONS

Lynch, "Analysis of the Mechanisms Underlying the Age-related Impairment in Long-Term Potentiation in the Rat," Reviews in the Neurosciences, vol. 9, pp. 169-201 (1998).

Anderson et al., "Breast-feeding and cognitive development: a meta-analysis," Am. J. Clin. Nutr., vol. 70, pp. 525-535, (1999).

Crawford, "The role of essential fatty acids in neural development: implications for perinatal nutrition," Am. J. Clin. Nutr., pp. 703S-710S, vol. 57 (suppl) (1993).

Crawford et al., "Are deficits of arachidonic and docosahexaenoic acids responsible for the neural and vascular complications of preterm babies?," Am. J. Clin, Nutr., vol. 68 (suppl), pp. 1032S-1041S (1997).

Hempenius et al., "Preliminary Safety Assessment of an Arachidonic Acid-enriched Oil derived from Mortierella alpina: Summary of Toxicological Data," Food and Chemical Toxicology, vol. 35, pp. 573-581 (1997).

Birch et al., "A randomized controlled trial of early dietary supply of long-chain polyunsaturated fatty acids and mental development in term infants," Developmental Medicine & Child Neurology, vol. 42, pp. 174-181 (2000).

Kalmijn et al., "Dietary Fat Intake and the Risk of Incident Dementia in the Rotterdam Study," Annals of Neurology, pp. 776-782 (1997).

Soderberg et al., "Fatty Acid Composition of Brain Phospholipids in Aging and in Alzheimer's Disease," Lipids, vol. 26, No. 6, pp. 421-425 (1991).

Ferguson, Letter to Linda Kahl, Ph.D., Aug. 3, 2001, "Re: GRAS Notice for ARASCO® (arachidonic acid-rich single-cell oil) Level in Term Infant Formula".

Wieraszko, "Avian Hippocampus as a Model to Sudy Spatial Orientation-Related Synaptic Plasticity," Molecular and Cellular Mechanisms of Neuronal Plasticity, pp. 107-129 (1998).

Notice of Opposition against EP1419768 by Abbott Laboratories (May 17, 2012).

Notice of Opposition against EP1419768 by N.V. Nutricia (May 16, 2012).

Fields, Letter to Food and Drug Administration, Aug. 27, 1998, "Re: Notice of a Claim for Exemption From Premarket Approval," available at http://www.accessdata.fda.gov/scripts/fcn/gras_notices/grn_7.pdf, documents created in 1998.

Randolph, "Repeatable Battery for the Assessment of Neuropsychological Status (RBANSTM)," available at http://www.pearsonassessments.com/HAIWEB/Cultures/en-us/Productdetail.htm?Pid=015-8166-000 (last visited Jul. 3, 2012).

D.A. Kharkevich, Farmakologiya [Pharmacology], M., Meditsina, 1987, pp. 41-42. (In Russian).

V.G. Belikov, Farmatsevticheskaya khimiya, [Pharmaceutical Chemistry], M., Vysshaya shkola, 1993, vol. 1, pp. 43-47. (In Russian).

Written Opinion mailed Nov. 7, 2006 in International PCT Application PCT/JP2006/313444 filed Jun. 29, 2006.

Office Action mailed Jan. 26, 2010 in Russian Application No. 2008103361/15(003664) with English language translation.

Search Report dated Nov. 7, 2006 for International Application No. PCT/JP2006/313444 filed Jun. 29, 2006.

Louis-Joseph Auguste et al., "Prevention of Stress-Induced Erosive Gastritis by Parenteral Administration of Arachidonic Acid", Journal of Parenteral and Enteral Nutrition, vol. 14, No. 6, 1990, pp. 615-617.

Search Report dated Jul. 20, 2005 for International Patent Application No. PCT/JP2005/005622 filed Mar. 18, 2005.

John R. Burgess et al.; "Long-Chain Polyunsaturated Fatty Acids in Children With Attention-Deficit Hyperactivity Disorder"; American Journal of Clinical Nutrition, Bethesda, MD, US, vol. 71, No. 1, Suppl, Jan. 2000, pp. 237S-330S; XP008000462.

Search Report dated Jul. 11, 2005 from International PCT Application No. PCT/JP2005/005623.

Search Report dated Jan. 31, 2007 for International Application No. PCT/JP2006/313437 filed Jun. 29, 2006.

Database WPI Week 200064, Derwent Publications Ltd., London, GB; AN 2000-658544, XP002410776.

Choi-Kwon, Smi et al., "Temporal changes in cerebral antioxidant enzyme activities after ischemia and reperfusion in a rat focal brain ischemia model: effect of dietary fish oil," Developmental Brain Research, Aug. 18, 2004, pp. 11-18, vol. 152, No. 1, XP007901417.

Supplementary European Search Report dated Aug. 30, 2010, issued in European patent application No. 04 79 3331.

Kark et al., "Adipose Tissue n-6 Fatty Acids and Acute Myocardial Infarction in a Population Consuming a Diet High in Polyunsaturated Fatty Acids", Am J Clin Nutr, 77, 796-802 (2003).

Panlab, s.I.u., "Water maze test".

McNamara et al., "The Neuropharmacological and Neurochemical Basis of Place Learning in the Morris Water Water Maze," Brain Res. Rev., vol. 18, pp. 33-49 (1993).

Reddy, "Preclinical and Clincal Behavioral Paradigms for Testing Drugs that Affect Learning and Memory Processes," Methods Find. Exp. Clin. Pharmacol. vol. 20, No. 3, pp. 249-277 (1998).

McGahon et al., "Age-Related Changes in Synaptic Function: Analysis of the Effect of Dietary Supplementation with Ω-3 Fatty Acids," Neuroscience, vol. 94, No. 1, 1999, pp. 305-314.

Office Action dated Jun. 28, 2010 in European Patent Application 03 748 553.9.

Gorelick et al., "Stroke Prevention Therapy Beyond Antithrombotics: Unifying Mechanisms in Ischemic Stroke Pathogenesis and Implications for Therapy: An Invited Review," Stroke; pp. 862-875.

Science Daily, "Brain Atrophy in Elderly Leads to Unintended Racism, Depression and Problem Gambling," Association for Psychological Sciences, 2007.

Yuksel et al., "Evaluation of mental retardation—Part 1: Etiologic classification of 4659 patients with mental retardation or multiple congenital abnormality and mental retardation," J. Pediatr. Neurosci, vol. 2, (2007), pp. 45-52.

Office Action dated Sep. 3, 2010 in Russian Patent Application No. 2008103361/15(003664) (with English translation).

Psychiatry edited by R. Sheider, Moscow, Praktika, 1998, pp. 280-282 and 287-289 (with English Translation).

The Merck Manual, Fifteenth Edition 1987, pp. 1421-1424.

Simopoulos, "Essential fatty acids in health and chronic disease," Am. J. Clin, Nutr, (1999), vol. 70, pp. 560S-569S.

Happe et al., "Time to give up on a single explanation for autism," Nature Neuroscience, vol. 9, No. 10, Oct. 2006, pp. 1218-1220.

Vericel et al., "The influence of low intake of n-3 fatty acids on platelets in elderly people," Atherosclerosis, vol. 147, (1999) pp. 187-192.

Nakawatase et al., "Alzheimer's Disease and Related Ementias," Cecil's Textbook of Medicine (Twenty-First Edition, vol. 1) W.B. Saunders Company, 2000, pp. 2042-2045.

Hart et al. "The Contribution of Risk Factors to Stroke Differentials, by Socioeconomic Position in Adulthood: The Renfrew/Paisley Study," Am. J. of Public Health, vol. 90, No. 11 (Nov. 2000), pp. 1788-1791.

"Cerebral Arteriosclerosis" National Institutes of Health, Nucleus Medical, 2 pages.

Vance [Editor], Biochemistry of Lipids and Membranes, 1985, pp. 330-331.

Belmonte et al., "Fragile X syndrome and autism at the intersection of genetic and neural networks," Nat. Neurosci., vol. 9, No. 10, (Oct. 2006), pp. 1221-1225.

Office Action dated Jun. 8, 2010 in Japanese Patent Application JP2004-539481 (in Japanese).

Kelley et al., "Arachidonic Acid Supplementation Enhances Synthesis of Eicosanoids Without Suppressing Immune Functions in Young Healthy Men," Lipids, vol. 33, No. 2 (1998) pp. 125-130.

Lynch et al., "Impaired Spatial Memory in Aged Rates is Associated with Alterations in Inositol Phospholipid Metabolism," NeuroReport, vol. 5, 1994, pp. 1493-1497, Lippincott Williams & Wilkins, London, England.

Wainwright et al., "Water Maze Performance is Unaffected in Artificially Reared Rats Fed Diets Supplemented with Arachidonic Acid and Docosahexaenoic Acid," J. Nutr., vol. 129, 1999, pp. 1079-1089, American Society for Nutritional Sciences, Bethesda, MD.

Wainwright et al., Arachidonic Acid Offsets the Effects on Mouse Brain and Behavior of a Diet with a Low (n-6):(n-3) Ratio and Very High Levels of Docosahexaenoic Acid, J. Nutr., vol. 127, 1997, pp. 184-193, American Society for Nutritional Sciences, Bethesda, MD.

Youdim et al., "Essential Fatty Acids and the Brain: Possible Health Implications," Int. J. Dev. Neurosci., vol. 18, 2000, pp. 383-399, Oxford Elsevier Science, New York, NY (Abstract Only).

Kawashima et al., "Enzymatic Synthesis of High-Purity Structured Lipids with Caprylic Acid at 1,3-Positions and Polyunsaturated Fatty Acid at 2-Position," J. Am. Oil Chem. Soc., vol. 78, 2001, pp. 611-616, American Oil Chemists Society, Champaign, IL.

Mackay & Mochly-Rosen, "Arachidonic Acid Protects Neonatal Rat Cardiac Myocytes from Ischaemic Injury though ε Protein Kinase C," Cardiovascular Res. vol. 50, 2001, pp. 65-74, Elsevier Science B.V., Amsterdam, Holland.

Horrobin, "Abnormal Membrane Concentrations of 20 and 22-Carbon Essential Fatty Acids: A Common Link Between Risk Factors and Coronary and Peripheral Vascular Disease," Prostaglandins Leukot. Essent. Fatty Acids, vol. 53, 1995, pp. 385-396, Churchill Livingstone, Edinburgh, Scotland.

Webster's Third New International Dictionary, 1963, p. 1798, G.& C. Merriam Co., Springfield, MA.

Strub, "Vascular Dementia," South. Med. J., vol. 96, 2003, pp. 363-366, Southern Medical Association, Birmingham, AL.

McGahon et al., "The Ability of Aged Rats to Sustain Long-Term Potentiation is Restored When the Age-Related Decrease in Membrane Arachidonic Acid Concentration is Reversed", Neuroscience, vol. 81, (1997), pp. 9-16.

Koletzko et al., "Polyunsaturated fatty acids in human milk and their role in early infant development," Journal of Mammary Gland Biology and Neoplasia, Jul. 1999, pp. 269-294, vol. 4, No. 3.

Carlson S.E., "Docosahexaenoic acid and arachidonic acid in infant development," Seminars in Neonatology, Oct. 2001, pp. 437-449, vol. 6, No. 5.

Auestad et al., "Visual, cognitive, and language assessments at 39 months: a follow-up study of children fed formulas containing long-chain polyunsaturated fatty acids to 1 year of age," Pediatrics, Sep. 2003, pp. e177-e183, vol. 112, No. 3, Pt 1.

Willatts et al., "Effect of Long-Chain Polyunsaturated Fatty Acids in Infant Formula on Problem Solving at 10 Months of Age," Lancet, vol. 352, 1998, pp. 688-691, Lancet, Publishing Group, London, England.

Lucas et al., "Efficacy and safety of long-chain polyunsaturated fatty acid supplementation of infant-formula milk: a randomized trial, "Lancet, Dec. 4, 1999, pp. 1948-1954, vol. 354 No. 9194.

Office Action dated Oct. 16, 2008 in Canadian Patent Application No. 2,456,049.

Office Action dated Mar. 2, 2010 in Japanese Patent Application No. 2004-539481 (In Japanese).

Kotani et al. "Improvement of Synaptic plasticity in the hippocampus of aged rats by ingestion of arachidonic acid," 24th Japan Neurosurgical Society Program, (2001), p. 243. (In Japanese w/English translation.

Novel Food Information—DHASCO® and ARASCO® from Health Canada, Date Modified Jan. 31, 2003.

Office Action issued Jan. 4, 2011, in Japanese Patent Application No. 2009-147715 (in Japanese).

Song et al., "Effects of dietary n-3 or n-6 fatty acids on interleukin-1β-induced anxiety, stress, and inflammatory responses in rats," J. Lipid Res. Oct. 2003, vol. 44, No. 10, pp. 1984-1991 (electronically published Jul. 1, 2003).

Mills et al., "Psychosocial stress, catecholamines, and essential fatty acid metabolism in rats," Proc. Soc. Exp. Biol. Med. Jan. 1994, vol. 205, No. 1, pp. 56-61.

Office Action dated Jan. 18, 2011 issued in Japanese Patent Application. No. 2004-271927 (In Japanese).

Kawashima et al., "Enzymatic Synthesis of High-Purity Structured Lipids with Caprylic Acid at 1,3-Positions and Polyunsaturated Fatty Acid at 2-Position," JAOCS, vol. 78, No. 6 (2001).

Office Action dated Jan. 11, 2011 issued in Japanese Patent Application. No. 2001-235519 (In Japanese).

Wollan et al., "Dietary essential fatty acids and gender-specific difference in rat maze learning and memory," Neuroscience Abstract, 2000, No. 793.13, Society for Neuroscience, vol. 26.

Office Action issued Feb. 17, 2011 in Chinese Patent Application. No. 200480001751.X (with English translation).

Taiwanese Office Action Issued Mar. 24, 2011 in Taiwanese Patent Application No. 092126198 (in Chinese).

European Office Action issued May 2, 2011 in European Patent Application No. 06780813.9.

Ulmann et al., "Brain and hippocampus fatty acid composition in phospholipid classes of aged-relative cognitive deficit rats," Prostaglandins, Leukotrienes and Essential Fatty Acids, vol. 64, Issue 3, Mar. 2001 (abstract).

The Merck Manual of Diagnosis and Therapy, 18th Ed., Merck Research Laboratories, 2006, pp. 1816-1818.

Japanese Office Action issued Jul. 19, 2011 in JP 2005-191506 (in Japanese).

K. Naliwaiko et al., "Effects of Fish Oil on the Central Nervous System: A New Potential Antidepressant?," Nutritional Neuroscience, vol. 7, No. 2 (Apr. 2004), pp. 91-99.

Golfetto et al., "Treatment of hemorrhagic stroke with arachidonic acid," Nutr. Neurosci., 2001, 4(1), 75-79, abstract.

Japanese Office Action dated Jul. 12, 2011 issued in JP Application No. 2004-271958 (in Japanese).

Yakkyoku (Pharmacy), 2000, vol. 51, No. 2, p. 2-10 (w/ partial English Translation).

Modern Physician, 2002, vol. 22, No. 9, p. 1155-1157 (w/ partial English translation).

Japanese Office Action dated Aug. 9, 2011 issued in JP Application No. 2005-191624 (in Japanese).

M. Minami et al., "Dietary Docosahexaenoic Acid Increases Cerebral Acetylcholine Levels and Improves Passive Avoidance performance in Stroke-Prone Spontaneously Hypertensive Rats," Pharmacology Biochemistry and Behavior, vol. 58, No. 4, pp. 1123-1129 (1997).

Russian Office Action issued Sep. 14, 2011 in Russian Application No. 2008103361/15(003664) (w/ English translation).

Bolshaya Rossijskaya Entsyclopediya, 1992, vol. 3, p. 202 (w/ English translation).

Korean Office Action issued Sep. 27, 2011 in Korean patent application No. 7005102/2005 (w/ English translation).

Gordon, "Nutrition and cognitive function," Brain & Development 19 (1997) pp. 165-170.

Office Action dated Sep. 22, 2011 issued in Australian Patent Application No. 2005283697.

Stevens et al., "EFA Supplementation in Children with Inattention Hyperactivity, and Other Disruptive Behaviors," Lipids, vol. 38, No. 10, (2003), pp. 1007-1021.

* cited by examiner

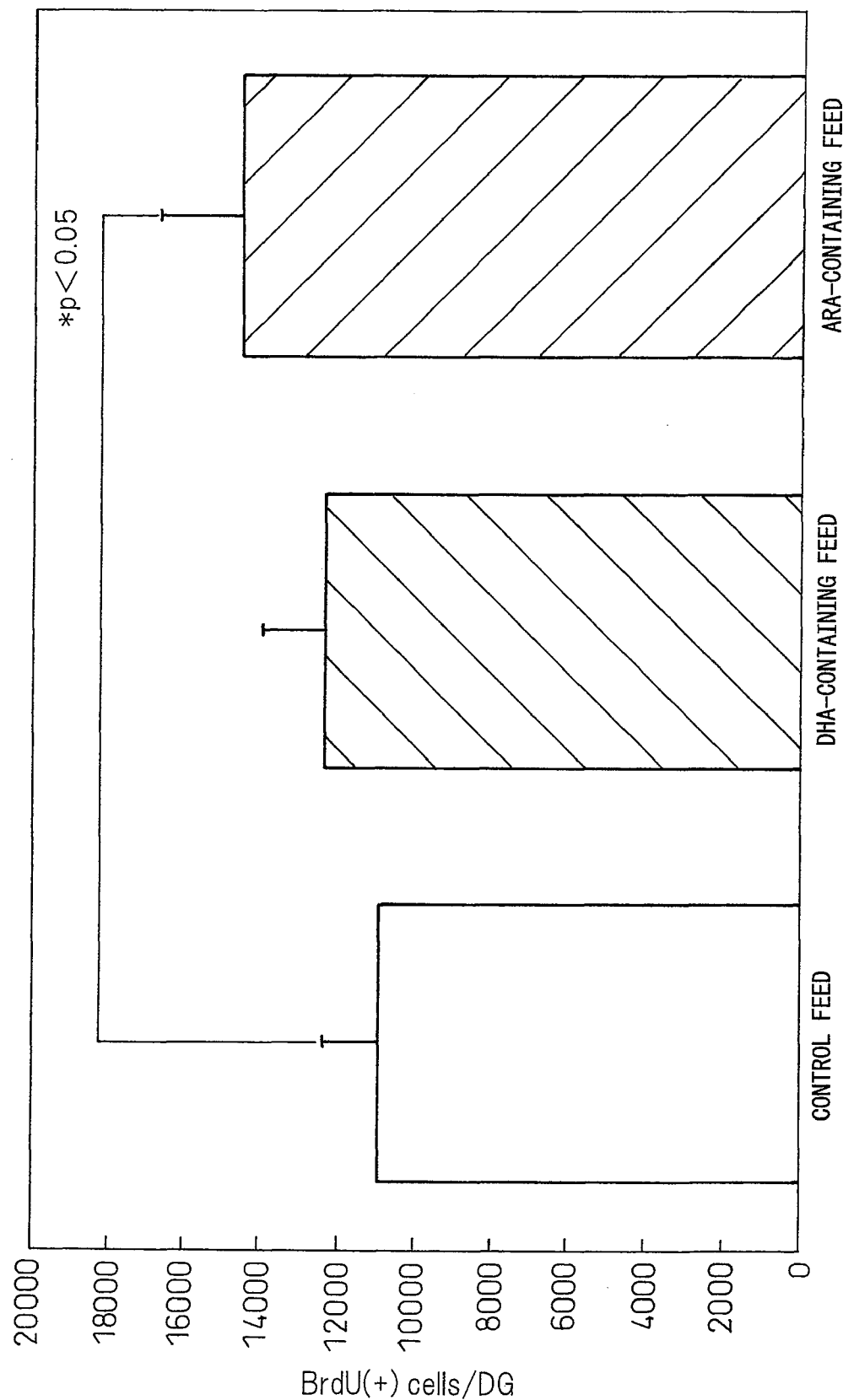

NERVE-REGENERATING AGENT

CROSS REFERENCE TO RELATED APPLICATIONS

This application is a National Stage of International Application No. PCT/JP2007/075403 filed Dec. 27, 2007, and which claims benefit of Japanese Patent Application No. 2006-355854 filed Dec. 28, 2006, which is incorporated herein in its entirety.

TECHNICAL FIELD

The present invention relates to a nerve-regenerating agent comprising, as an active ingredient, arachidonic acid and/or a compound containing arachidonic acid as a constituent fatty acid.

BACKGROUND ART

Neurological disorders (for example, Parkinson's disease, Alzheimer's disease, polyglutamine diseases (Huntington's disease, spinocerebellar degeneration and the like), amyotrophic lateral sclerosis, polyneuropathy, spinal cord injury and cerebrovascular disease) occur as a result of degeneration, reduction or cell death of cerebral or peripheral neurons due to aging or environmental or genetic factors, or as a result of injury or removal. Effective treatments for such neurological disorders therefore include replenishment of neurotransmitters lost by the damaged neurons, or regeneration of the neurons. Sources of neurotransmitters include undifferentiated neural stem cells, and ES cells which are capable of differentiating to many different cell types.

However, because very few endogenous neural stem cells are capable of differentiating into nerves and it is not possible to sufficiently replenish cells that have degenerated due to cerebrovascular disease or the like, it is necessary to rely on external sources (specifically fetal neural stem cells or human ES cells), whereby ethical and transplantative antigenic problems may arise. Moreover, no techniques have been established for reliable differentiation into neurons, and their functions have not been successfully regenerated. In addition, regenerative medicine, which is concerned with regeneration of the central nervous system, has not been widely employed because of the problems inherent with its use of aborted fetal brains.

Recently, however, growth of new neurons (known as "neurogenesis") in the hippocampus of adult brains has been reported. This has led to research toward methods for treating neurological disorders by stimulation of neural stem cells in the brains of patients, using drugs and the like, to induce their regeneration (for example, fibroblast growth factor-2 (Non-patent document 1) and NGF (Non-patent document 2)). However, since all such proteins or proteinaceous factors must be injected into the brain and are therefore difficult to employ for general medical treatment, low molecular compound substitutes for these proteins such as salvianolic acid B (Patent document 1) and lithium or its pharmacologically acceptable salts (Patent document 2) have been proposed.

Moreover, recently published reports describe confirmed augmentation of neurogenesis in the hippocampus when mother mice are loaded with taurine by oral administration, fetal mice are loaded via the breast milk, and neuronal development is observed by intraabdominal administration of BrdU (Non-patent document 3). In addition, it has been reported that administration of DHA (docosahexaenoic acid) to third-generation DHA-deficient aged rats promotes neurogenesis in the hippocampus (Non-patent document 4). A correlation has also been found between depression and reduced neurogenesis.

On the other hand, it has been demonstrated that arachidonic acid and/or compounds containing arachidonic acid as a constituent fatty acid improve symptoms of reduced brain function, and specifically, when aged animals are examined with a Morris water maze test, the reduced learning ability that accompanies aging is improved by administration of arachidonic acid and/or compounds containing arachidonic acid as a constituent fatty acid (Patent document 3).

Patent document 1: Japanese Unexamined Patent Publication No. 2006-76948
Patent document 2: International Patent Publication No. WO2004/91663
Patent document 3: Japanese Unexamined Patent Publication No. 2003-48831
Non-patent document 1: Pro. Nat. Acad. Sci. USA, 5874-5879 (2001)
Non-patent document 2: Cell, 110, 429 (2002)
Non-patent document 3: Program of the 173rd Meeting of the Essential Amino Acid Research Council, p. 1, 2003
Non-patent document 4: Neuroscience, 139, 991-997 (2006)

DISCLOSURE OF THE INVENTION

It is an object of the present invention to provide an easily applicable nerve-regenerating agent.

As a result of much diligent research directed toward solving the problems described above, the present inventors have found that hippocampal neurogenesis is augmented in infant rats when mother rats are loaded with triglycerides containing arachidonic acid (defined as triglycerides that include triglycerides wherein all or a portion of the constituent fatty acids consist of arachidonic acid) by oral administration, and their infant rats are loaded via the breast milk. Furthermore, an effect was confirmed against depression and Alzheimer-type dementia to a more notable level than with DHA, which is reported to have a neurogenesis effect, and the invention was completed based on these findings.

Thus, the present invention provides a nerve-regenerating agent comprising, as an active ingredient, arachidonic acid and/or a compound containing arachidonic acid as a constituent fatty acid. The nerve-regenerating agent may be used, for example, as a therapeutic agent for neuropsychiatric disorders. As neuropsychiatric disorders there may be mentioned amyotrophic lateral sclerosis, Parkinson's disease, cognitive disorder, Alzheimer's disease, cerebrovascular disease, apoplexy, spinal cord injury, Huntington's disease, anxiety disorder, ataxia, depression, manic depressive psychosis, impaired development, attention deficit/hyperactivity disorder and learning disorder.

The nerve-regenerating agent is preferably used for oral administration.

The aforementioned compound containing arachidonic acid as a constituent fatty acid may be, for example, an alcohol ester of arachidonic acid, or a triglyceride, phospholipid or glycolipid wherein all or a portion of the constituent fatty acid consists of arachidonic acid.

BRIEF DESCRIPTION OF THE DRAWINGS

FIG. 1 is a graph showing a comparison of neurogenesis in rats given feed without arachidonic acid (control), rats given feed with arachidonic acid and rats given feed with docosahexanoic acid.

BEST MODE FOR CARRYING OUT THE INVENTION

The present invention relates to a nerve-regenerating agent comprising, as an active ingredient, arachidonic acid and/or a compound containing arachidonic acid as a constituent fatty acid.

The nerve-regenerating agent of the invention is useful not only for humans but also for non-human animals. A "non-human animal" is an industrial animal, pet or experimental animal, and more specifically, an "industrial animal" is a farm animal such as a cow, horse, pig, goat, sheep, or a race horse, hunting dog or the like, a "pet" is a dog, cat, marmoset, hamster or the like, and an "experimental animal" is an animal used in research in the field of medical, biology, agriculture or pharmacy, such as a mouse, rat, guinea pig, beagle, minipig, rhesus monkey, cynomolgus monkey or the like, although there is no limitation to those mentioned above. Preferred non-human animals are animals that are raised as pets, such as dogs or cats.

A "nerve-regenerating agent" according to the invention is an agent having an effect of promoting neurogenesis by acting on neural stem cells in a human or animal brain, thus increasing the number of neurons in the brain (also referred to as "neurogenesis promoter" throughout the present specification). The nerve-regenerating agent of the invention can be used as a prophylactic and/or therapeutic agent for neuropsychiatric disorder associated with nerve degeneration or damage. As neuropsychiatric disorders there may be mentioned not only neurodegenerative conditions such as Parkinson's disease, cognitive disorder, Alzheimer's disease, polyglutamine diseases (Huntington's disease, spinocerebellar degeneration and the like), amyotrophic lateral sclerosis, polyneuropathy, spinal cord injury, cerebrovascular disease and apoplexy, but also conditions not associated with nerve degeneration such as anxiety disorder, ataxia, depression and manic depressive psychosis, or impaired development (pervasive developmental disorders (PDD), attention deficit/hyperactivity disorder (AD/HD), learning disorder (LD)), and the like.

The nerve-regenerating agent of the invention may be used alone in the simple form of arachidonic acid and/or a compound containing arachidonic acid as a constituent fatty acid, but for most purposes it is preferably provided as a medical preparation. When provided as a medical preparation, it may be formulated as a mixture with one or more optional pharmacologically acceptable components. The method of formulation may be one commonly employed in the technical field, and for example, it may be a method listed in the Japanese Pharmacopeia, or a similar method.

When the agent is used as a medical preparation, the route of administration may be oral or parenteral, such as intravenous, selected based on the maximum effect for treatment, although oral administration is most preferred. The dosage form may be appropriately selected from among enteral nutrient preparations, powders, granules, tablets, capsules, troches, internal solutions, suspensions, emulsions, syrups and injections.

When the invention is used as a medical preparation, the amount of the arachidonic acid and/or the compound containing arachidonic acid as a constituent fatty acid, added as an active ingredient, is not particularly restricted so long as the object of the invention is achieved, and an appropriate mixing proportion may be used. The dose of the medical preparation will depend on the patient age, body weight and symptoms and the frequency of administration, and for example, the arachidonic acid or compound containing arachidonic acid as a constituent fatty acid according to the invention will usually be administered at about 0.001 g-10 g, preferably about 0.01 g-1 g, more preferably about 0.05-0.5 g and most preferably about 0.1 g-0.3 g, per day for an adult (approximately 60 kg) based on the amount of arachidonic acid, divided into 1-3 administrations per day.

Since the nerve-regenerating agent of the invention exhibits its effect by oral administration, the arachidonic acid and/or the compound containing arachidonic acid as a constituent fatty acid may be used alone or in combination with a food or beverage that either contains substantially no or very little arachidonic acid, and provided as a food or beverage with a prophylactic or ameliorating effect against neuropsychiatric disorder.

The "food or beverage" may be a general food, or a functional food, specified health food, nutritional supplement, modified milk for premature infants, modified milk for infants, infant food, maternal food or geriatric food, or an animal food or beverage including pet supplements (animal nutritional supplements). Such foods and beverages include those marketed with indication or labeling on food composition wrapping containers and/or in the tools (for example, pamphlets) for marketing of food compositions, as having effects of prevention and/or amelioration of neuropsychiatric disorders, and specifically prevention or amelioration of affective disorders (for example, depression) or intellectual impairment (for example, Alzheimer-type dementia or cerebrovascular disease dementia), forgetfulness prevention, cognitive disorder prevention or mental age rejuvenation.

The foods and beverages may be used as fat or oil containing food products including, for example, natural food products that naturally contain fats and oils, such as meat, fish or nuts, food products to which fats and oils are added during preparation, such as soups, food products for which fats and oils are used as heating media, such as doughnuts, fat and oil food products such as butter, processed foods to which fats and oils are added during processing, such as cookies, or food products that are sprayed or coated with fats and oils during final processing, such as hard biscuits, as well as fat- and oil-free agricultural food products, fermented food products, livestock food products and aquatic food products, or they may be optionally added to beverages, with no limitation whatsoever to the form of use. Thus, additives and the like commonly used in various food products may also be included. In particular, antioxidants are preferably included to prevent oxidative degradation of the active ingredient of the invention.

As examples of antioxidants there may be mentioned natural antioxidants such as tocopherols, flavone derivatives, phyllodulcins, kojic acid, gallic acid derivatives, catechins, fukiic acid, gossypol, pyrazine derivative, sesame lignans (sesamin, episesamin, sesaminol, sesamol and the like), guaiacol, guaiacum oil, p-coumarinic acid, nordihydroguaiaretic acid, sterols, terpenes, nucleotides, nucleic acid bases, carotenoids and lignans, and synthetic antioxidants, typical of which are ascorbyl palmitate esters, ascorbyl stearate esters, butylhydroxyanisole (BHA), butylhydroxytoluene, (BHT), mono-t-butylhydroquinone (TBHQ) and 4-hydroxymethyl-2,6-di-t-butylphenol (HMBP).

As tocopherols there may be mentioned α-tocopherol, β-tocopherol, γ-tocopherol, δ-tocopherol, ε-tocopherol, ξ-tocopherol, η-tocopherol and tocopherol esters (tocopherol acetate and the like). As examples of carotenoids there may be mentioned β-carotene, canthaxanthin, astaxanthin and the like.

In addition to these antioxidants there may be mentioned dissolving aids, buffering agents, dissolution accelerators, gelling agents, suspending agents, wheat flour, rice flour, starch, corn starch, polysaccharides, milk protein, collagen, rice oil, lecithin and various additives (for example, vitamins, sweeteners, organic acids, coloring agents, aromas, dehumidifying agents, fiber, electrolytes, minerals, nutrients, antioxidants, preservatives, aromatic agents, moistening agents, natural food extracts, vegetable extracts) and the like, without any particular limitation to these.

The main drug component of the arachidonic acid or compound containing arachidonic acid as a constituent fatty acid is arachidonic acid. The daily consumption of arachidonic acid from diet has been reported as 0.14 g in the Kanto region and 0.19-0.20 g in the Kansai region of Japan (Shishitsu Eiyougaku [Lipid Nutrition] 4, 73-82, 1995), but the elderly, considering their reduced lipid consumption and reduced pancreatic lipase activity, require an equivalent or greater amount of arachidonic acid intake. Consequently, the daily consumption of the arachidonic acid or compound containing arachidonic acid as a constituent fatty acid according to the invention is 0.001 g-10 g, preferably 0.01 g-1 g, more preferably 0.05-0.5 g and most preferably 0.1 g-0.3 g for adults (for example, with a body weight of 60 kg), based on arachidonic acid.

It is known that the major fatty acids in phospholipid membranes of the brain are arachidonic acid and docosahexaenoic acid. Docosahexaenoic acid has also been reported to have an effect against Alzheimer-type dementia, and animal tests have reportedly shown a neurogenesis effect dependent on docosahexaenoic acid intake (Non-patent document 4). The animal test results are the results observed for administration of docosahexaenoic acid after raising on docosahexaenoic acid-deficient feed over a period of three generations, and this cannot be considered the normal state. However, the present inventors have found that when immature rats are given arachidonic acid-containing feed or docosahexaenoic acid-containing feed via breast milk under normal raising conditions, using the immature rats soon after birth, significant neurogenesis occurs in the brains (hippocampus) of the immature rats given the arachidonic acid-containing feed.

The neurogenesis-promoting effect and neuropsychiatric disorder curative effect of the invention can be evaluated by the following neuron detection method.

Bromodeoxyuridine (BrdU) that allows labeling of proliferating cells or a retrovirus vector that can express a gene which allows labeling of cells such as Green Fluorescent Protein (GFP) or β-galactosidase, is administered to the experimental animal during, before or after initial administration of the substance of interest, and the substance is administered once or several times a day for a raising period of 7-28 days. Next, the experimental animal is perfusion-fixed, the brain is extracted and a frozen section of the brain is prepared and observed under a fluorescent microscope, and when using BrdU as the labeling agent for proliferating cells, for example, the number of BrdU-positive cells per unit area and the proportion of the number of NeuN, Calretinin, Calbindin and Tuj1 positive cells as neuron markers with respect to the number of BrdU-positive cells are compared to the negative control.

EXAMPLES

The present invention will now be explained in greater detail by examples. However, the invention is not limited to the examples described below.

Reference Example 1

Production of Arachidonic Acid-Containing Triglycerides

*Mortierella alpina* CBS754.68 was used as an arachidonic acid-producing strain. After preparing 6 kL of medium containing 1.8% glucose, 3.1% defatted soybean flour, 0.1% soybean oil, 0.3% $KH_2PO_4$, 0.1% $Na_2SO_4$, 0.05% $CaCl_2.2H_2O$ and 0.05% $MgCl_2.6H_2O$ in a 10 kL culturing vat, the initial pH was adjusted to 6.0.

A 30 L portion of the pre-culture solution was seeded, and aerated agitation culture was carried out for 8 days under conditions with a temperature of 26° C., an aeration rate of 360 $m^3$/hr and a vat internal pressure of 200 kPa. The agitation rate was adjusted to maintain a dissolved oxygen concentration of 10-15 ppm. Also, the glucose concentration in the medium was kept within a range of 1-2.5% up to the 4th day and 0.5-1% thereafter (the percentage values being based on weight (w/v) %), by feeding. Upon completion of the culturing, the cells that contained the arachidonic acid-containing triglycerides were recovered by filtration and drying, the fat and oil component was extracted from the obtained cells with hexane, and edible fat and oil purification steps (degumming, deacidification, deodorization, decoloration) were carried out to obtain 150 kg of arachidonic acid-containing triglycerides (with arachidonic acid bonded at any position of the triglycerides).

The obtained fats and oils (triglycerides) were methyl esterified and the obtained fatty acid methyl esters were analyzed by gas chromatography, by which the proportion of arachidonic acid among the total fatty acids was determined to be 40.84 wt %. The palmitic acid, stearic acid, oleic acid, linolic acid, γ-linolenic acid and dihomo-γ-linolenic acid contents were 11.63, 7.45, 7.73, 9.14, 2.23 and 3.27 wt %, respectively. The arachidonic acid-containing fats and oils (triglycerides) were also ethyl esterified, and 99 wt % arachidonic acid ethyl ester was separated and purified from the fatty acid ethyl ester mixture containing 40 wt % arachidonic acid ethyl ester using established high-performance liquid chromatography, to produce arachidonic acid-containing triglycerides (SUNTGA40S).

Example 1

Effect of Arachidonic Acid-Containing Fat and Oil Intake on Hippocampal Neurogenesis in Juvenile Animals The juvenile animals used were 2-day-old rats. Upon dividing 30 juvenile rats into 3 groups: a control feed intake group (10 rats: Control), an arachidonic acid-containing feed intake group (10 rats: ARA) and a DHA-containing feed intake group (10 rats: DHA), each group was given the control feed, SUNTGA40S-containing feed (Example 1 product) or DHA-containing fat and oil feed as shown in Table 1, and the rats were raised for 4 weeks. The arachidonic acid content of the arachidonic acid-containing feed and the DHA content of the DHA-containing feed were equal. Since pups cannot directly ingest food up to the 3rd week after birth, the mothers were administered the feed (freely available), and the pups (juvenile rats) were given the arachidonic acid via breast milk.

After 4 weeks of raising, 50 mg/kg BrdU (bromodeoxyuridine) was intraperitoneally injected into the juvenile rats 3 times during a day. On the following day, the brains were extracted and frozen sections were prepared covering the entire hippocampus region in the direction of the rostrum, and anti-BrdU antibody was used for immunostaining prior to fluorescent microscope observation. An exact 1/6 portion of the entire frozen section was removed and the number of BrdU-labeled cells in the hippocampal dentate gyrus neurogenesis region was counted and multiplied by 6 to calculate the number of BrdU-labeled cells in the entire hippocampus, in order to determine the neural stem cell and neural precursor cell proliferation potency.

TABLE 1

|  | Control feed (g) | Arachidonic acid-containing feed (g) | DHA-containing feed (g) |
|---|---|---|---|
| Casein | 200 | 200 | 200 |
| DL-Methionine | 3 | 3 | 3 |
| Corn starch | 150 | 150 | 150 |
| Sucrose | 500 | 500 | 500 |
| Cellulose powder | 50 | 50 | 50 |
| Corn oil | 50 | 50 | 50 |
| Minerals AIN-76 | 35 | 35 | 35 |
| Vitamins AIN-76 | 10 | 10 | 10 |
| Choline tartrate | 2 | 2 | 2 |
| Vitamin E | 0.05 | 0.05 | 0.05 |
| SUNTGA40S | 0 | 5 | 0 |
| DHA-containing fat and oil | 0 | 0 | 5 |

FIG. 1 shows the measurement results for each of the immature rats. New growth of neurons (augmented neurogenesis) is clearly seen in the arachidonic acid-containing feed intake group (ARA) compared to the control feed intake group (Control) and DHA-containing feed intake group (DHA). As a result of determining the mean value for each group, a significant increase of 133% was found in the arachidonic acid-containing feed intake group, with 100% as the BrdU uptake in the control feed intake group.

INDUSTRIAL APPLICABILITY

The nerve-regenerating agent or neural stem cell neurogenesis promoter of the invention is characterized by being orally administered. It can be easily utilized since it does not require surgical operation for intracerebral injection as is common in the prior art. Furthermore, because it is in an orally administered form, the agent of the invention can provide novel compositions for prevention of neuropsychiatric disorders, since an effect is exhibited not only as a therapeutic agent for targeted therapy of neuropsychiatric disorders, but also from the viewpoint of preventive medicine.

What is claimed is:

1. A method of regenerating nerves in a subject with a neuropsychiatric disorder not associated with nerve degeneration comprising administering a composition comprising a compound containing arachidonic acid as a constituent fatty acid to said subject in an amount of 0.001-10 g (based on arachidonic acid); wherein the compound containing arachidonic acid as a constituent fatty acid is an alcohol ester of arachidonic acid, a triglyceride, phospholipid, or glycolipid, wherein all or a portion of the constituent fatty acid consists of arachidonic acid, and wherein the neuropsychiatric disorder is ataxia.

2. The method of claim 1, wherein the composition is administered orally.

3. The method of claim 1, wherein the compound containing arachidonic acid as a constituent fatty acid is a triglyceride, and wherein all or a portion of the constituent fatty acid consists of arachidonic acid.

4. The method of claim 1, wherein said compound is administered in an amount of 0.01 g-1 g (based on arachidonic acid).

5. The method of claim 1, wherein said compound is administered in an amount of 0.05 g-0.5 g (based on arachidonic acid).

6. The method of claim 1, wherein said compound is administered in an amount of 0.1-0.3 g (based on arachidonic acid).

* * * * *